(12) United States Patent
Rabe et al.

(10) Patent No.: US 10,059,715 B2
(45) Date of Patent: Aug. 28, 2018

(54) ACID ADDITION SALT OF IBRUTINIB

(71) Applicant: ratiopharm GmbH, Ulm (DE)

(72) Inventors: Sebastian Rabe, Ulm (DE); Manfred Erdmann, Neu-Ulm (DE); Wolfgang Albrecht, Ulm (DE)

(73) Assignee: Ratiopharm GmbH, Ulm (DE)

( * ) Notice: Subject to any disclaimer, the term of this patent is extended or adjusted under 35 U.S.C. 154(b) by 0 days.

(21) Appl. No.: 15/516,285

(22) PCT Filed: Aug. 25, 2015

(86) PCT No.: PCT/EP2015/069430
§ 371 (c)(1),
(2) Date: Mar. 31, 2017

(87) PCT Pub. No.: WO2016/050422
PCT Pub. Date: Apr. 7, 2016

(65) Prior Publication Data
US 2017/0305914 A1    Oct. 26, 2017

(30) Foreign Application Priority Data
Oct. 1, 2014    (EP) .................................... 14187387

(51) Int. Cl.
A01N 43/90    (2006.01)
A61K 31/519    (2006.01)
C07D 487/04    (2006.01)

(52) U.S. Cl.
CPC ........ *C07D 487/04* (2013.01); *C07B 2200/13* (2013.01)

(58) Field of Classification Search
CPC .......................... C07D 487/04; A61K 31/519
USPC ....................................... 514/262.1; 544/262
See application file for complete search history.

(56) References Cited

FOREIGN PATENT DOCUMENTS

| EP | 2 650 294 A1 | 10/2013 |
| WO | WO 2011/046964 | 4/2011 |
| WO | WO 2013/184572 | 12/2013 |
| WO | WO 2014/004707 | 1/2014 |

OTHER PUBLICATIONS

Bastin, et. al., Organic Process Research & Development 2000, 4, 427-435.*
Stahl, et. al. Handbook of Pharmaceutical Salts, (2002), 1-374.*

* cited by examiner

*Primary Examiner* — Jeffrey H Murray
(74) *Attorney, Agent, or Firm* — Chalin A. Smith; Smith Patent, LLC

(57) ABSTRACT

The present invention relates to acid addition salts of ibrutinib, a pharmaceutical composition comprising the same as well as a method of preparing the same.

14 Claims, 13 Drawing Sheets

ACID ADDITION SALT OF IBRUTINIB

PRIORITY

This application corresponds to the U.S. national phase of International Application No. PCT/EP2015/069430, filed Aug. 25, 2015, which, in turn, claims priority to European Patent Application No. 14.187387.7 filed Oct. 1, 2014, the contents of which are incorporated by reference herein in their entirety.

FIELD OF THE INVENTION

The present invention relates to acid addition salts of ibrutinib, a method of preparing the same as well as a pharmaceutical composition comprising the same.

BACKGROUND OF THE INVENTION

Ibrutinib (1-[(3R)-3[4-Amino-3-(4-phenoxyphenyl)-1H-pyrazolo[3,4-d]pyrimidin-1-yl] piperidin-1-yl]prop-2-en-1one) has the following chemical structure (I):

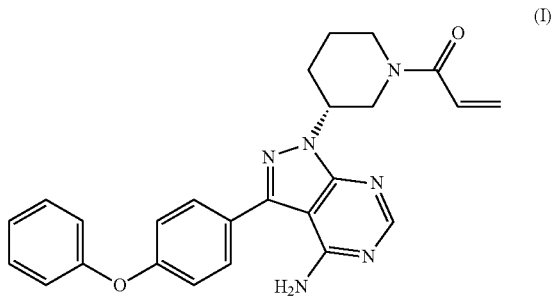 [SMILES: C=CC(=O)N1CCC[C@@H](n2nc(-c3ccc(Oc4ccccc4)cc3)c3c(N)ncnc32)C1]

This pharmaceutically active ingredient is known from WO 2008/039218. Ibrutinib is an inhibitor of bruton's tyrosine kinase (BTK). BTK is a key mediator of at least three critical B-cell pro-survival mechanisms occurring in parallel regulating B-cell apoptosis, cell adhesion and lymphocyte migration and homing. By inhibiting BTK ibrutinib drives B-cells into apoptosis and/or disrupts cell immigration and adherence to tumor-protective microenvironments. Ibrunitib is therefore suitable for treating chronic lymphocytic leukemia (CLL) and small lymphocytic lymphoma (SLL) which are B-cell non-hodgkin lymphomas (NHL). It is marketed in the US under the name Imbruvica.

Crystalline polymorphic forms of ibrutinib are disclosed in WO 2013/184572.

Pharmaceutical formulations comprising ibrutinib are disclosed in WO 2014/004707A1.

Ibrutinib has a very low solubility in water e.g. form A of ibrutinib shows according to WO 2013/184572, an observed aqueous solubility of only about 0.013 mg/ml at about pH 8. The solubility strongly depends on the pH. This results in problems in the bioavailability of the active ingredient, first because of the low solubility, and second its solubility depends on the pH value in the stomach of the patient. Particular problems arise from patients wherein the pH value is altered, e.g. due to physiological variability, diseases or premedication such as PP-inhibitors. Therefore, there is a need for oral pharmaceutical compositions that contain ibrutinib in a form which is highly soluble and thus provides a reliable bioavailability of the active ingredient.

As further forms of ibrutinib, both WO 2013/184572 and WO 2014/004707 generally disclose pharmaceutically acceptable salts of ibrutinib, including acid addition salts. However, none of these documents discloses any properties of specific salts. Further, none of these documents discloses methods how to obtain such salts, nor discloses that such salts have been obtained.

When one tries to prepare acid addition salts of ibrutinib following conventional procedures of the preparation of acid addition salts of pharmaceutical ingredients, high amounts of impurities are formed. That is, preparation of acid addition salts by a conventional method is not suitable for the preparation of pharmaceutical products comprising this active ingredient.

SUMMARY OF THE INVENTION

It has now surprisingly been found that the above-mentioned and further problems are solved by a specific method of preparing acid addition salts of ibrutinib, which comprises cooling the solution of ibrutinib when adding the acid to obtain the acid addition salt. This method allows for the first time preparation of acid addition salts of ibrutinib with high purity suitable for pharmaceutical preparations. Further it seems that only strong acids with a low $pK_a$ (e.g. below about 2) are able to deprotonate ibrutinib to convert it into an acid addition salt.

Therefore the present invention relates to a method for preparing an acid addition salt of ibrutinib comprising the steps of a) dissolving ibrutinib in a suitable solvent, preferable an organic solvent, and b) contacting the obtained solution with the acid, wherein the solution of ibrutinib is cooled during addition of the acid. Preferably the method further comprises a step c) of precipitating the acid addition salt in a suitable antisolvent of the salt.

In the method of the present invention in step a) any suitable solvent for ibrutinib can be used which are known to the skilled person. Preferably, an organic solvent, more preferably a polar organic solvent, such as dichloromethane, chloroform, tetrahydrofurane (THF) or methanol can be used. Most preferably ibrutinib is dissolved in dichloromethane. The solution of ibrutinib is cooled before adding the acid in step b), and preferably during addition of the acid in step b). The temperature of the solution of ibrutinib in step b) is below room temperature (22° C.), preferably below 10° C., more preferably below 0° C., even more preferably below −5° C., in particular below −10° C., e.g. below −15° C., or even below −20° C.

In the method of the present invention in step b) the molar ratio of acid to ibrutinib is typically equal to or above 1, typically equal to or below 5, preferably in the range of 1 to 2, more preferably 1 to 1.5, even more preferred 1 to 1.3, in particular 1 to 1.2, e.g. about 1. In the method of the invention preferably the acid is added in step b) until these molar ratios are reached, preferably at the temperatures as defined above.

In step b) the solution of ibrutinib can be contacted with the acid following conventional procedures, preferably under stirring. Preferably the method of the invention is conducted under water-free conditions. Preferably, the acid is used in step b) is water-free in an organic solvent which may be the same or a different solvent as used for dissolving ibrutinib. The acids are typically commercially available in suitable organic solvents, e.g. hydrogen chloride in diethylether or isopropanol, which is preferably used according to the present invention to produce the preferred acid addition salt ibrutinib hydrochloride.

In a preferred embodiment the method of the present invention further comprises a step c) of precipitating the acid addition salt in a suitable antisolvent of the acid addition salt of ibrutinib. Suitable antisolvents of the acid addition salt are known to the skilled person. Preferably as antisolvent a weak polar or nonpolar organic solvent, such as methyl tert.-butylether (MTBE), diethylether, n-hexane or n-heptane is used. Also preferred as antisolvents are $C_3$-$C_6$ alcohols, such as isopropanol. Most preferably the acid addition salt of ibrutinib is precipitated by addition of MTBE or isopropanol. The addition of the antisolvent is preferably performed under vigorous stirring. Preferably step c) is conducted at a temperature of below room temperature (22° C.), preferably below 10° C., more preferably below 0° C., even more preferably below −5° C., in particular below −10° C., e.g. below −15° C., or even below −20° C. Most preferably the same temperature is used in step c), i.e. precipitating the acid addition salt, which is also used in step b), i.e. contacting the solution of ibrutinib with the acid. Cooling in step c) has been found to be advantageous for the preparation of the precipitate of the acid addition salt of ibrutinib, as the precipitate can be easily removed from the solution and shows advantageous flowability characteristics.

DETAILED DESCRIPTION OF THE PREFERRED EMBODIMENTS

Figure 1A:
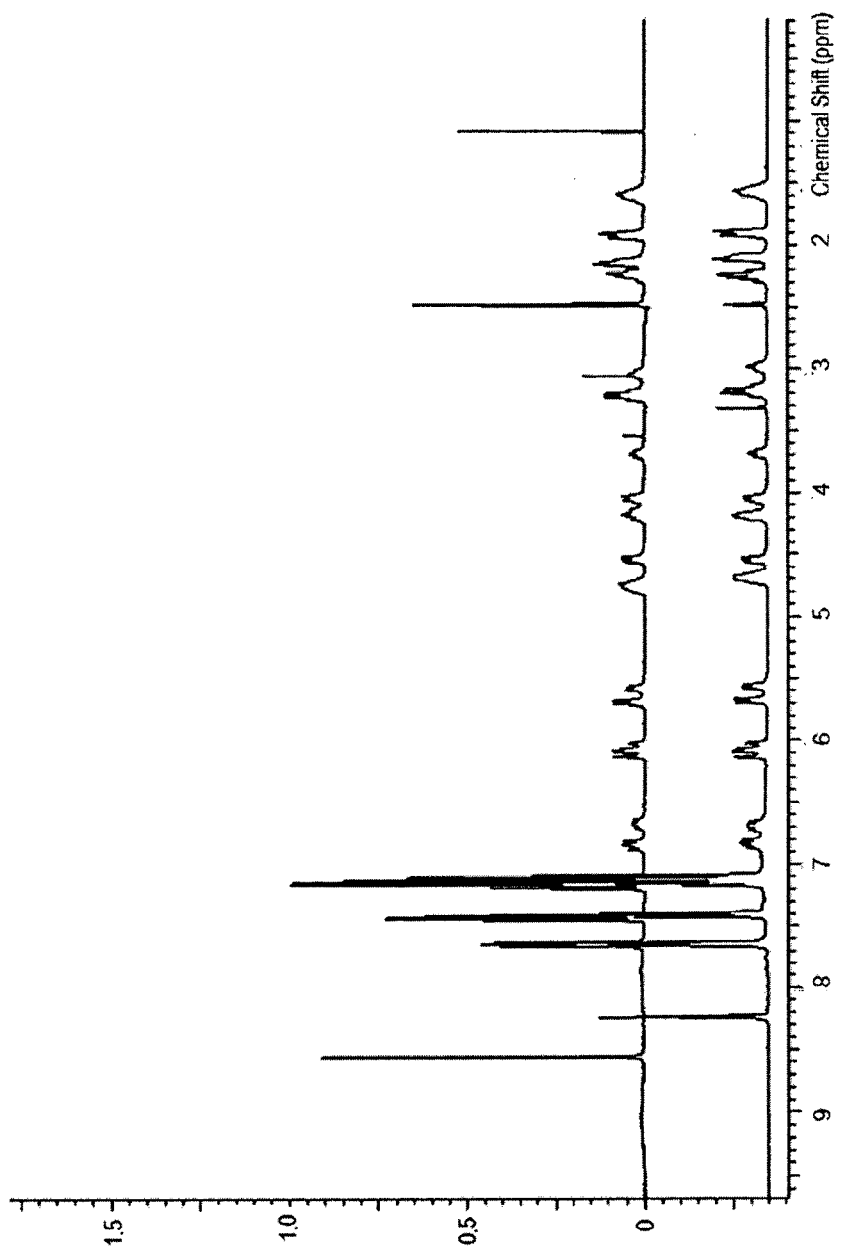
FIG. 1a shows the $^1$H-NMR spectrum of ibrutinib hydrochloride (upper graph) compared to the $^1$H-NMR spectrum of ibrutinib free base (lower graph) ($^1$H-NMR in DMSO-$d_6$, 400 MHz).

The method of the present invention surprisingly allows preparing acid addition salts of ibrutinib with very high purity, in particular suitable for pharmaceutical compositions, which also have an improved solubility compared to ibrutinib free base.

Therefore, the present invention also relates to acid addition salts of ibrutinib having a high purity, in particular suitable for pharmaceutical compositions, of at least 99.0%, preferably at least 99.5% more preferably at least 99.8%, in particular at least 99.9%. Purity can be determined by HPLC/UV (as defined below) and is expressed in [area-%] at the wavelength of the UV detection of $\lambda$=230 nm. Preferably the same purity, i.e. of at least 99.0%, preferably at least 99.5% more preferably at least 99.8%, in particular at least 99.9% is achieved in [area-%] at the wavelength of the UV detection of $\lambda$=254 nm.

The acid addition salts of ibrutinib can be prepared with known acids for the preparation of pharmaceutical acceptable salts. Preferably, inorganic acids are used such as hydrochloric acid or hydrobromic acid, most preferably hydrochloric acid is used. Preferably, the p$K_a$ of the acid used is equal to or below 3, in particular below 1.

It has been found that when acid addition salts of ibrutinib are prepared according to known processes for the preparation of acid addition salts under conventional conditions, e.g. addition of acids to ibrutinib in a suitable solvent at room temperature, impurities are formed, which seem to be reaction products of an nucleophilic addition of the acid at the acrylic double bond of ibrutinib. It has further been found by the inventors that increasing the temperature during or after addition of the acid led to nearly quantitative preparation of the addition reaction product of the acid with the acrylic double bond of ibrutinib. On the other side, the inventors found that cooling the solution during the step of adding the acid to the solution of ibrutinib allows preparation of the acid addition salt with high purity, and in particular with very low content of the addition reaction product.

Therefore, the present invention also relates to acid addition salts of ibrutinib, in particular of the acids as defined in the above, wherein the content of the addition reaction product of the added acid with the acrylic double bond of ibrutinib is lower than 1% by weight, preferably lower than 0.5% by weight, more preferably by lower than 0.2% by weight, in particular lower than 0.1% by weight. In general the addition reaction product of the added acid with the acrylic double bond of ibrutinib has the chemical formula (IIa):

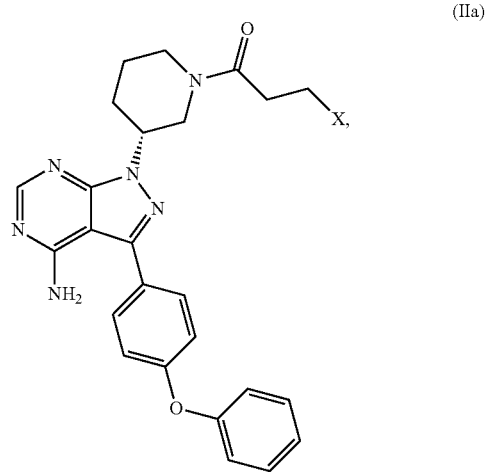

wherein residue X corresponds to the deprotonated acid, such as Cl or Br, respectively, preferably residue X is Cl.

It has further surprisingly been found that it seems that only two selected salts, namely the hydrochloride and the hydrobromide salt of ibrutinib, can be obtained in crystalline and in excellent pure state. This allows the preparation of an active pharmaceutical ingredient in good crystalline quality with advantageous handling properties such as good flowability, in particular suitable for pharmaceutical compositions, which also has an improved solubility compared to ibrutinib free base.

In a preferred embodiment the present invention relates to ibrutinib hydrochloride. Ibrutinib hydrochloride is characterized by a $^1$H-NMR spectrum showing the following signals: $^1$H NMR (400 MHz, DMSO-$d_6$) δ ppm 1.60 (m, 1H); 1.86-1.98 (m, 1H); 2.15 (m, 1H); 2.23 (m, 1H); 2.98-3.10 (m, 0.5H); 3.22 (m, 1H); 3.61-3.76 (m, 0.5H); 4.05 (m, 0.5H); 4.16 (m, 1H); 4.54 (m, 0.5H); 4.75 (m, 1H); 5.53-5.73 (m, 1H); 5.99-6.20 (m, 1H); 6.60-6.93 (m, 1H); 7.07-7.24 (m, 5H); 7.37-7.49 (m, 2H); 7.65 (d, J=8.21 Hz, 2H); 8.57 (s, 1H). A $^1$H-NMR spectrum of ibrutinib hydrochloride is shown in FIG. 1.

Figure 2:
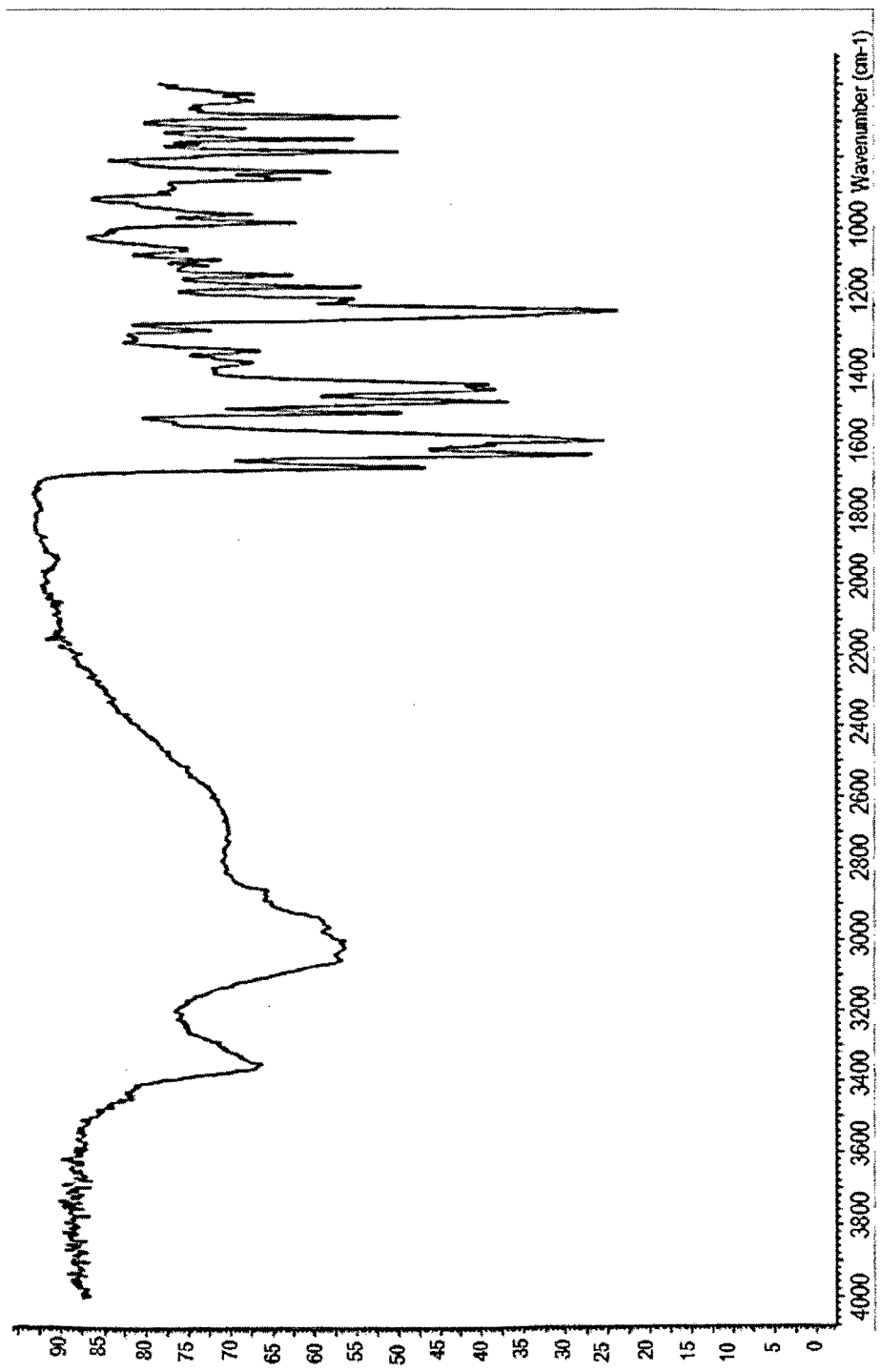
FIG. 2 shows an IR-spectrum of ibrutinib hydrochloride.

Ibrutinib hydrochloride is further characterized by an IR-spectrum showing the following peaks: 3350; 3001; 1676; 1637; 1614; 1599; 1518; 1489; 1452; 1439; 1346; 1232; 1200; 1165; 1134; 1092; 987; 964; 868; 847; 789; 754; 723; 692; 629 cm$^{-1}$. A IR-spectrum of ibrutinib hydrochloride is shown in FIG. 2.

It has been found that by the process of the invention ibrutinib hydrochloride can be prepared in excellent purity. Therefore, the present invention also relates to crystalline acid addition salts of ibrutinib, in particular, crystalline ibrutinib hydrochloride and crystalline ibrutinib hydrobromide. While ibrutinib base (Form A) is substantially insoluble at pH 4.5 and pH 6.8, ibrutinib hydrochloride has a solubility in water at 37° C. of 0.02 mg/ml and 0.05 mg/ml at pH 4.5 and pH 6.8 respectively (after 1 hour) and 0.46 mg/ml and 0.41 mg/ml at pH 4.5 and pH 6.8 respectively (after 24 hours).

Moreover as expected, ibrutinib base (form A) has increased solubility at pH 1.2 (in 0.1M HCl) of 2.07 mg/ml. However, crystalline ibrutinib hydrochloride has an unexpectedly high solubility at pH 1.2 (in 0.1M HCl) of 7.37 mg/ml.

This may result in a significantly increased bioavailability of the active ingredient.

In a preferred embodiment the present invention provides crystalline ibrutinib hydrochloride in a certain polymorphic form which shows an XRPD pattern having peaks at 9.8, 13.6, 15.1, 17.0 and 21.1 degrees 2-theta±0.2 degrees 2-theta or 9.8±0.1°2-θ, 15.3±0.1°2-θ, 21.1±0.1°2-θ, 22.6±0.1°2-θ and 24.3±0.1°2-θ. Further characteristic peaks are at 8.1, 8.2, 14.2, 19.9 and 28.9 degrees 2-theta±0.2 degrees 2-theta or 13.5±0.1°2-θ, 16.5±0.1°2-θ, 17.0±0.1°2-θ, 25.5±0.1°2-θ and 28.9±0.1°2-θ.

Figure 3:
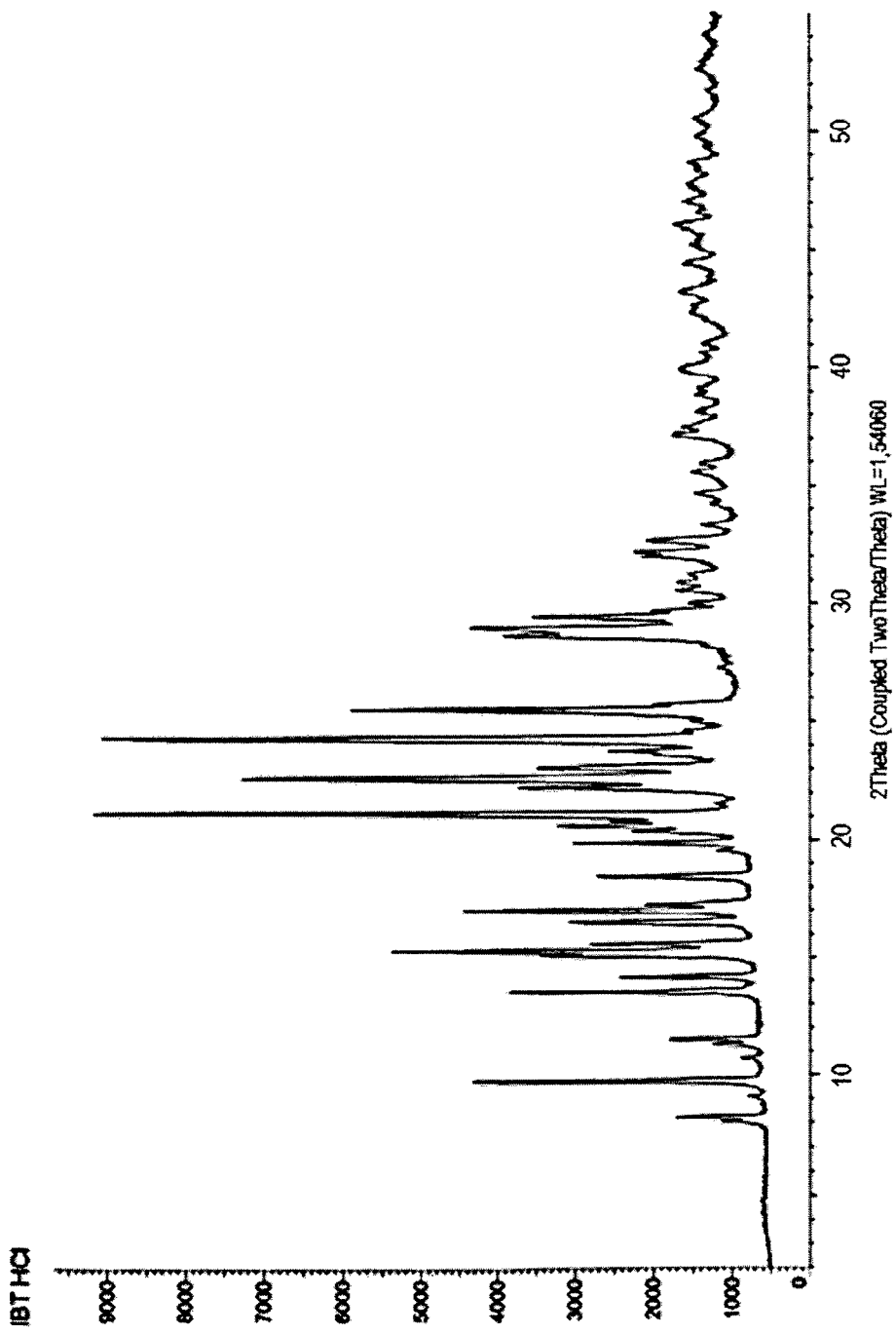
FIG. 3 shows an XRPD pattern of crystalline ibrutinib hydrochloride.

In a particular preferred embodiment the polymorphic crystalline form of ibrutinib hydrochloride of the present invention shows substantially the XRPD pattern of FIG. 3.

Figure 4:
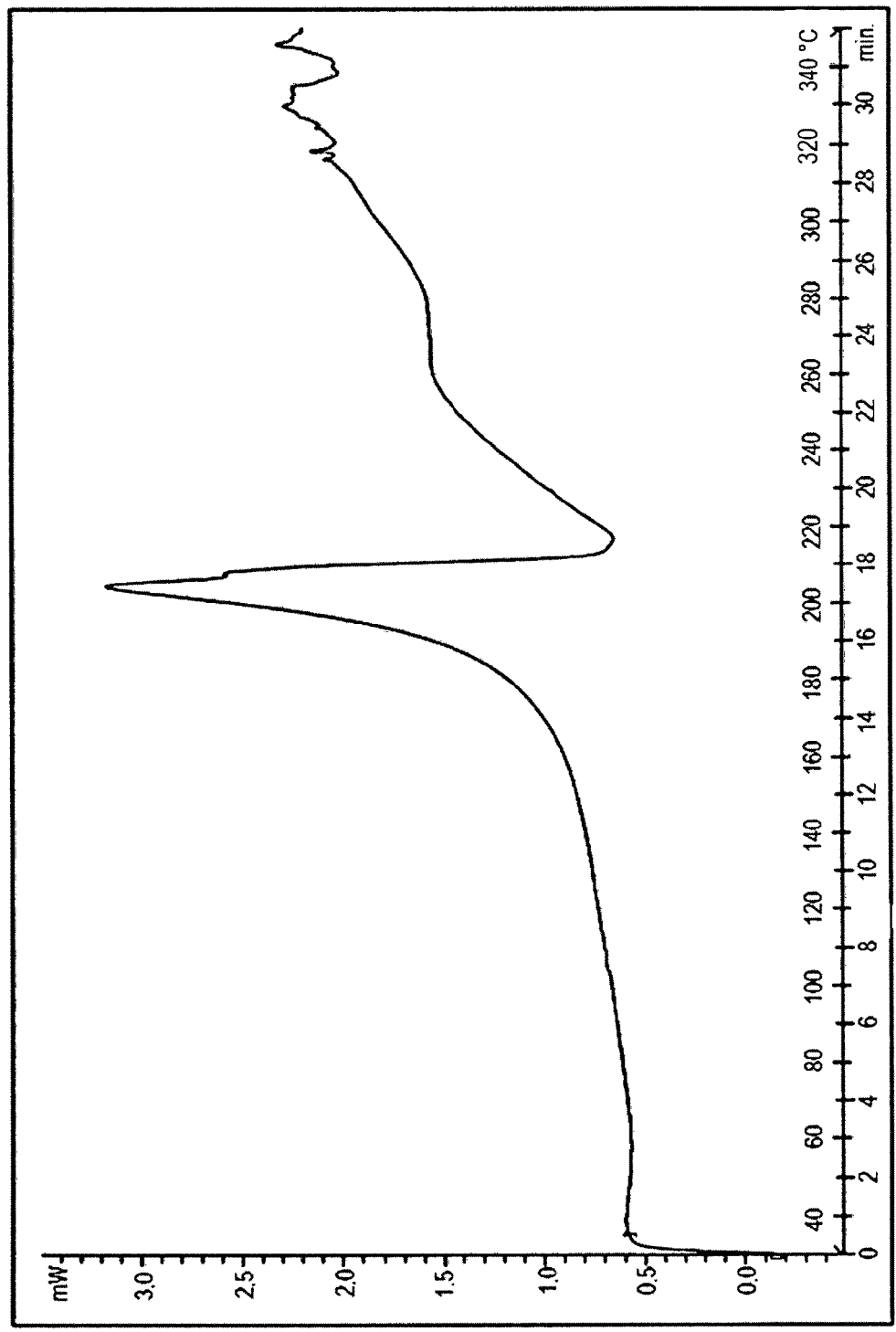
FIG. 4 shows a DSD thermogram of ibrutinib hydrochloride.

Crystalline ibrutinib hydrochloride according to the present invention is further characterized by a DSC thermogram showing a broad endotherm with an onset temperature of approx. 150° C. (±5° C.) and a peak temperature of 205° C. (±1° C.) followed by a broad exotherm with an onset temperature at 215° C. (±5° C.) and a peak temperature at 217° C. (±2° C.). A characteristic DSC thermogram is shown in FIG. 4.

Figure 8:
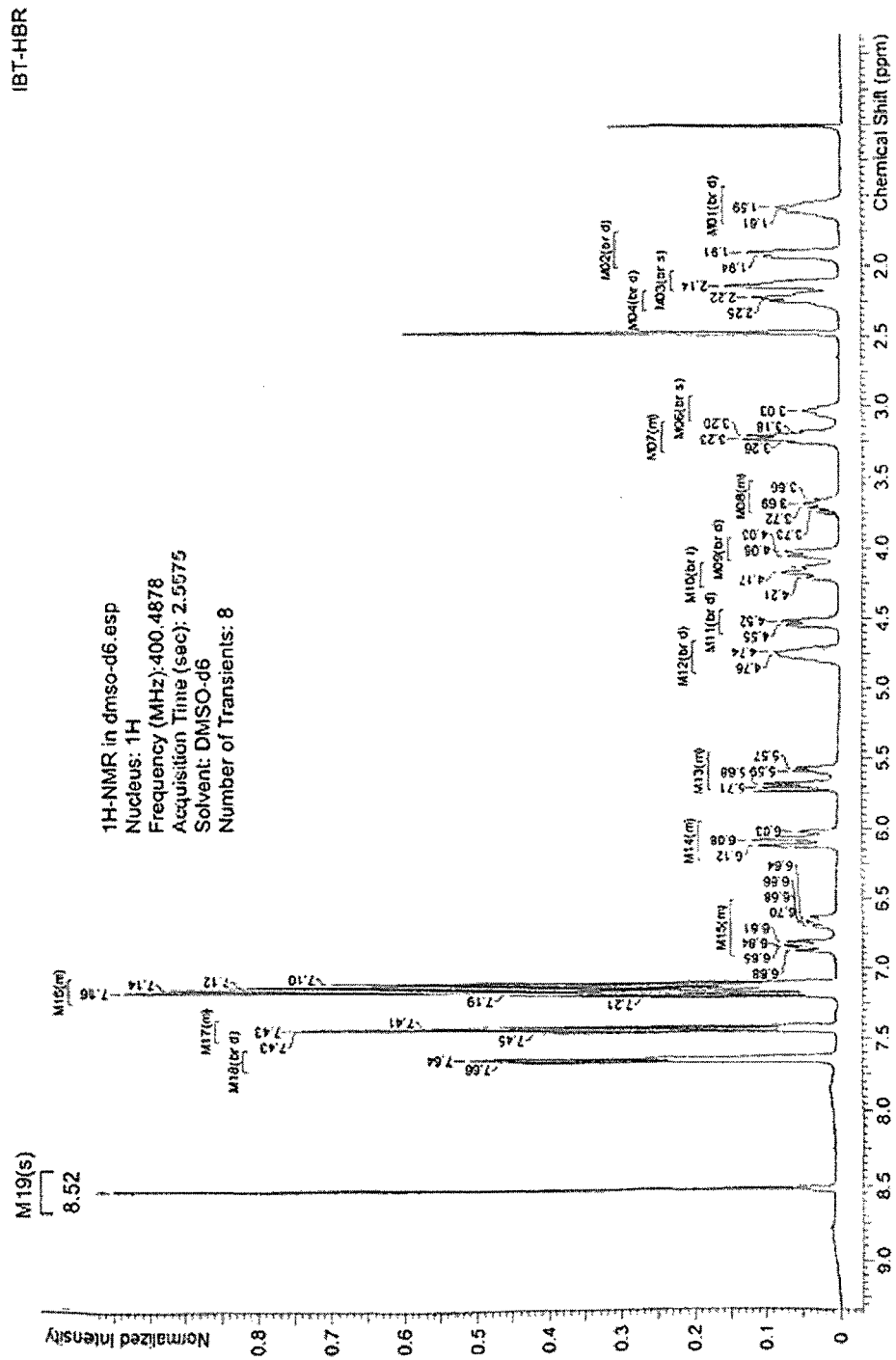
FIG. 8 shows the $^1$H-NMR spectrum of ibrutinib hydrobromide ($^1$H-NMR in DMSO-$d_6$, 400 MHz).

In a preferred embodiment the present invention relates to ibrutinib hydrobromide. Ibrutinib hydrobromide is characterized by a $^1$H-NMR spectrum showing the following signals: $^1$H NMR (400 MHz, DMSO-$d_6$) δ ppm 1.60 (m, 1H); 1.86-1.98 (m, 1H); 2.15 (m, 1H); 2.23 (m, 1H); 2.98-3.10 (m, 0.5H); 3.22 (m, 1H); 3.61-3.76 (m, 0.5H); 4.05 (m, 0.5H); 4.16 (m, 1H); 4.54 (m, 0.5H); 4.75 (m, 1H); 5.53-5.73 (m, 1H); 5.99-6.20 (m, 1H); 6.60-6.93 (m, 1H); 7.07-7.24 (m, 5H); 7.37-7.49 (m, 2H); 7.65 (d, J=8.21 Hz, 2H); 8.57 (s, 1H). $^1$H-NMR spectrum of ibrutinib hydrobromide is shown in FIG. 8.

In a preferred embodiment the present invention relates to ibrutinic hydrobromide, which is characterized by XRPD diffraction having peaks at 5.5, 18.1, 22.3, 24.5, and 26.9 degrees 2-theta±0.2 degrees 2-theta. Ibrutinib hydrobromide is further characterized by XRPD diffraction peaks at 12.3, 15.6, 18.3, 20.2, 21.6 and 24.4 degrees 2-theta±0.2 degrees 2-theta.

Figure 9:
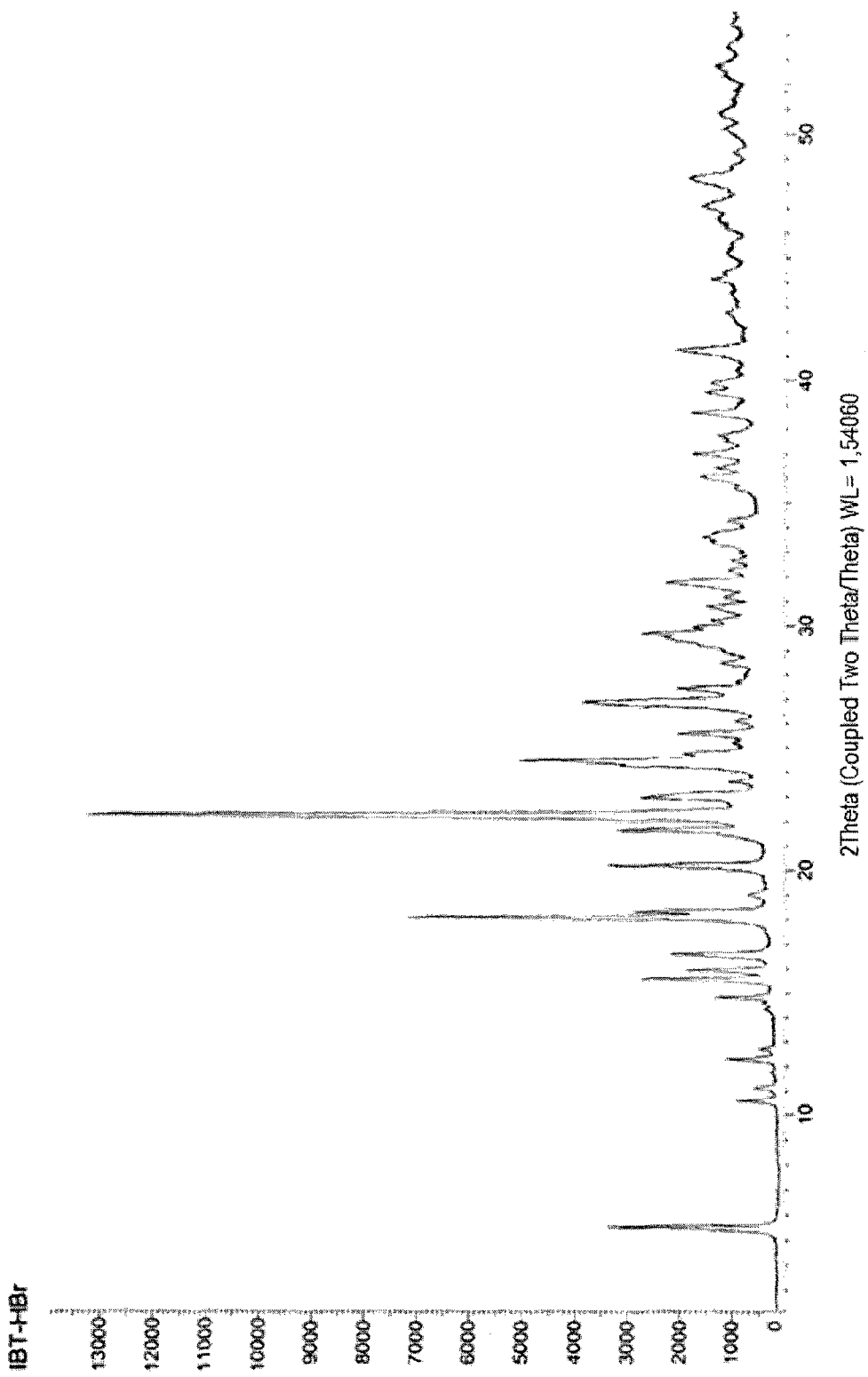
FIG. 9 shows an XRPD pattern of crystalline ibrutinib hydrobromide.

An XRPD diffraction pattern of ibrutinib hydrobromide is shown in FIG. 9.

As previously discussed inventors found that when acid addition salts of ibrutinib are prepared by processes under conventional conditions, impurities are formed. Not wishing to be bound by theory it seems that these impurities are generated by nucleophilic addition of the acid to the acrylic double-bond of ibrutinib. In order to confirm this theory, the chemical structure of an impurity was investigated, which is obtained when using hydrogen chloride as acid in order to prepare ibrutinib hydrochloride. The impurity was purified and investigated by mass spectrometry and $^1$H-NMR spectroscopy. The proposed chemical structure of the impurity as nucleophilic addition product of HCl to ibrutinib, is shown as the following formula (II):

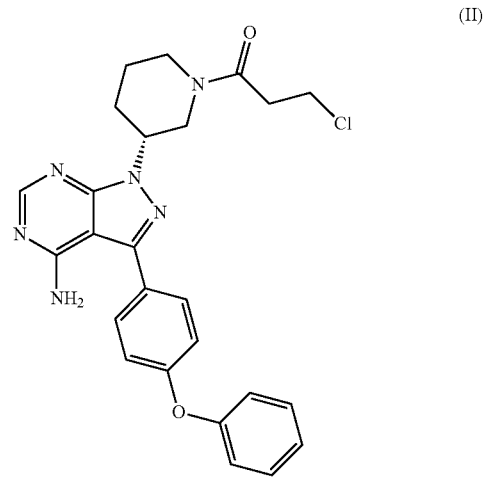 [SMILES: Nc1ncnc2c1c(-c1ccc(Oc3ccccc3)cc1)nn2[C@@H]1CCCN(C(=O)CCCl)C1]

(II)

Figure 5:
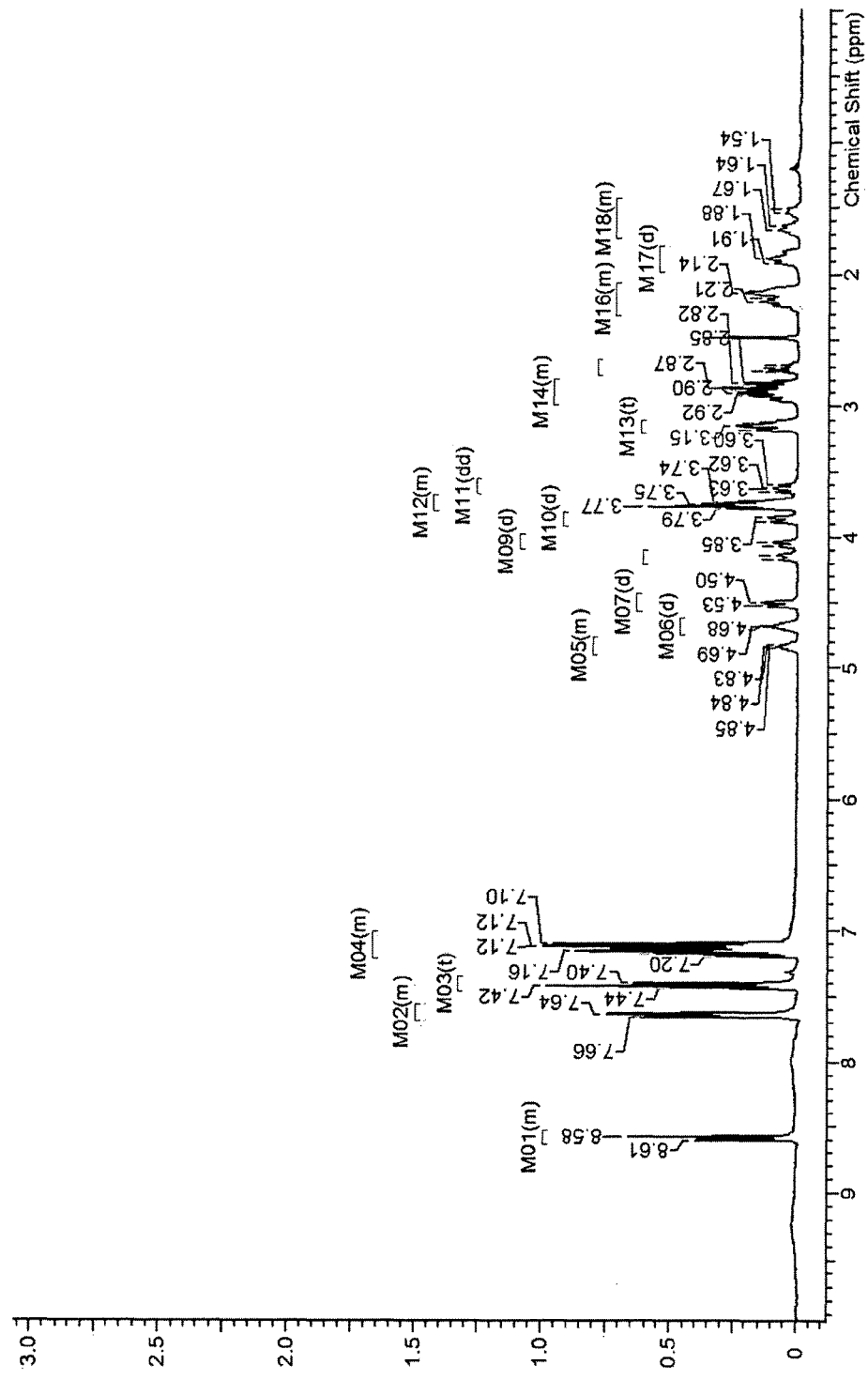
FIG. 5 shows an $^1$H-NMR spectrum of compound (II).
Figure 6:
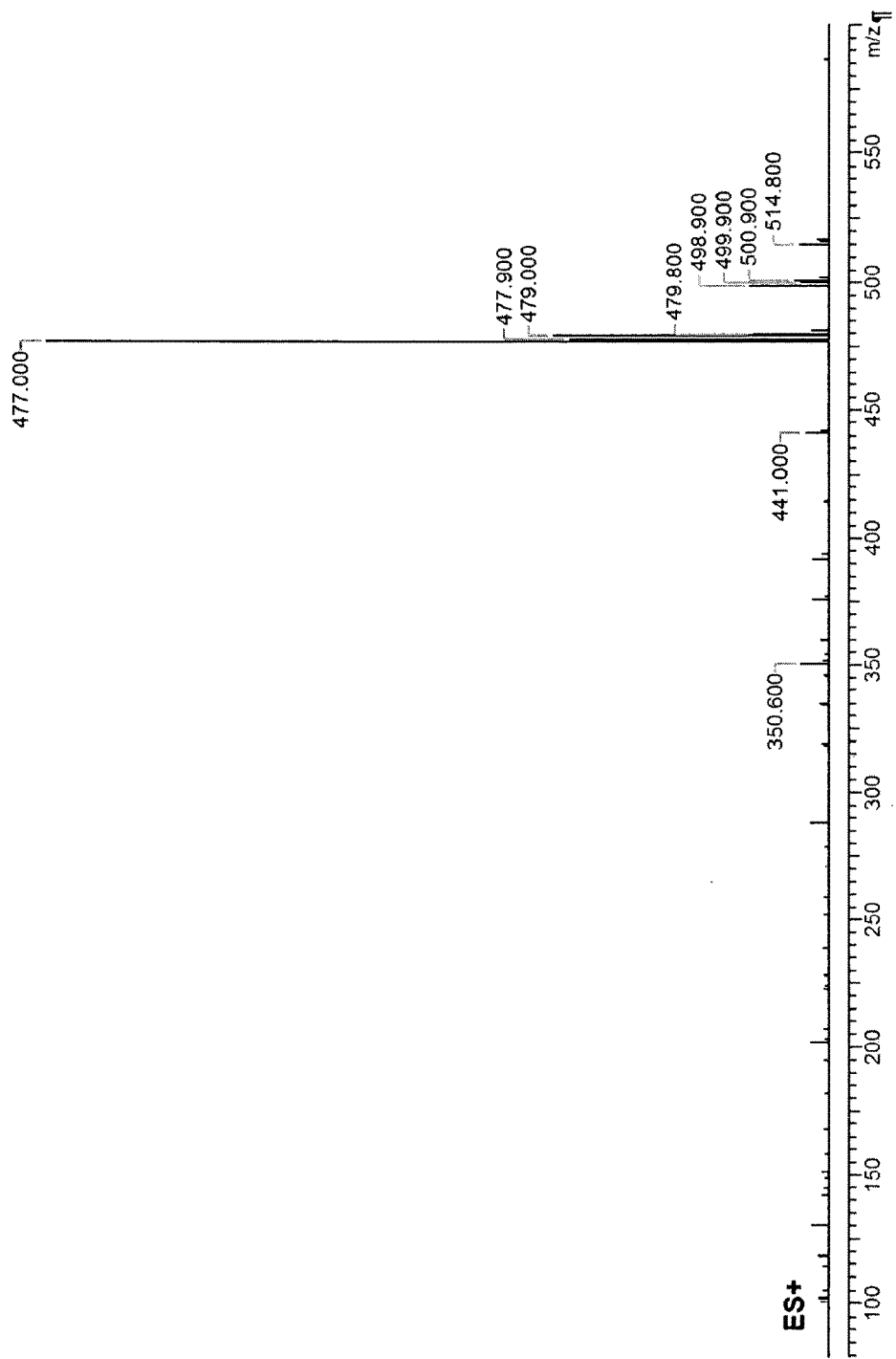
FIG. 6 shows a mass spectrum of compound (II).

The $^1$H-NMR spectrum of the compound formula (II), as shown in FIG. 5, comprises the following peaks $^1$H NMR (400 MHz, DMSO-$d_6$) δ ppm: 1.44-1.73 (m, 1H); 1.90 (m, 1H); 2.07-2.31 (m, 2H); 2.65-2.78 (m, 0.5H); 2.80-3.00 (m, 2H); 3.15 (m, 1H); 3.63 (m, 0.5H); 3.69-3.80 (m, 2H); 3.87 (m, 0.5H); 4.05 (m, 0.5H); 4.15 (m, 0.5H); 4.52 (m, 0.5H); 4.68 (m, 0.5H); 4.77-4.91 (m, 0.5H); 7.01-7.23 (m, 5H); 7.42 (m, 2H); 7.57-7.70 (m, 2H); 8.54-8.64 (m, 1H).

A compound of formula (II) can be obtained as impurity when preparing ibrutinib hydrochloride. Therefore a compound of formula (IIa), in particular a compound of formula (II), is suitable for the determination of the purity of ibrutinib and pharmaceutical formulations comprising ibrutinib, in particular when ibrutinib is in the form of an acid addition salt, such as those described above. Further these compounds of formula (IIa) and (II) are suitable in a method for the preparation of ibrutinib with high purity, in particular in a purity as defined above. Preferably the ibrutinib is in the form of an acid addition salt, in particular the acid addition salts as defined above.

Therefore the present invention relates to the use of a compound of formula (IIa), wherein X is Cl or Br, for determination of the purity of ibrutinib in a pharmaceutical formulation comprising ibrutinib, wherein preferably the ibrutinib is in the form of an acid addition salt. Further the present invention relates to the use of a compound of formula (IIa), wherein X is Cl or Br, in a method for the preparation of ibrutinib or a pharmaceutical formulation comprising ibrutinib with high purity, wherein preferably the ibrutinib is in the form of an acid additional salt.

The present invention furthermore relates for pharmaceutical preparation comprising an acid addition salt of ibrutinib according to the present invention, preferably the acid addition salt of ibrutinib with hydrochloric acid, in particular crystallized ibrutinib, e.g. the polymorphic form as defined above. The pharmaceutical preparation of the present invention preferably is an oral solid preparation, such as a capsule or tablet.

The pharmaceutical preparation can additionally contain one or more pharmaceutically acceptable excipients, such as fillers, binders, glidants, disintegrants, flow regulating agents and release agents. Suitable excipients are for example disclosed in "Lexikon der Hilfsstoffe für Pharmazie, Kosmetik und angrenzende Gebiete", published by H. P. Fielder, 4$^{th}$ Edition and "Handbook of Pharmaceutical Excipients", 3$^{rd}$ Edition, published by A. H. Kibbe, American Pharmaceutical Association, Washington, USA, and Pharmaceutical Press, London.

Suitable fillers are for example lactose and calcium hydrogen phosphate. Fillers can be present in an amount of 0-80% by weight, preferably in an amount of 10-60% by weight of the total weight of the composition.

Suitable binders are for example polyvinylpyrrolidone, hydroxypropyl cellulose, hydroxypropyl methylcellulose, methyl cellulose, hydroxyethyl cellulose, sugars, dextran, or corn starch. Binders can be present in an amount of 0-80% by weight, preferably in an amount of 10-60% by weight of the total weight of the composition.

Suitable glidants are for example alkaline earth metal salts of fatty acids, like stearic acid. The glidant can be present for example in an amount of 0-2% by weight, preferably in an amount of 0.5-1.5% by weight of the total weight of the composition.

Suitable disintegrants are for example crosscarmelose sodium, sodium carboxymethyl starch, crosslinked polyvinylpyrrolidone (crosspovidone), sodium carboxymethylglycolate (such as Explotab) and sodium bicarbonate. The disintegrant can be present in an amount of 0-20% by weight, preferably in an amount of 1-15% by weight of the total weight of the composition.

A suitable flow regulating agent is for example colloidal silica. The flow regulating agent can be present in an amount of 0-8% by weight, preferably in an amount of 0.1-3% by weight of the total weight of this composition.

A suitable release agent is for example talcum. The release agent can be present in an amount of 0-5% by weight, preferably in an amount of 0.5-3% by weight of the total weight of the composition.

The pharmaceutical preparation of the present invention can be prepared by methods well known to a person skilled in the art.

The invention will now be illustrated by the examples, which are not to be construed as limiting.

Analytical Methods $^1$H-NMR Spectroscopy

Instrument: Varian Mercury 400 Plus NMR Spectrometer, Oxford AS, 400 MHz.

HPLC/UV

Instrument: Agilent 1200
Injection volume: 5 µl
Solvent A: acetonitrile
Solvent B: 0.001M KH$_2$PO$_4$
Flow: 1.5 ml/min
Temperature: RT
Column: Discovery C18, 150*4.6 mm, 5 µm

| time [min] | solvent B [%] |
|---|---|
| 0.00 | 75 |
| 8.00 | 40 |
| 13.00 | 40 |
| 14.00 | 75 |
| 17.00 | 75 |

LCMS

Instrument: Agilent 1260 Infinity
Injection volume: 2 µl
Solvent A: acetonitrile
Solvent B: water+0.1% formic acid+0.05% heptafluorobutyric acid
Flow: 1 ml/min
Temperature: 40° C.
Column: Phenomenex Kinetex 2.6 µm C18 100A 150*4.6 mm 2.6 µm
Mass instrument: Agilent 6110 Quadrupol LC/MS

| time [min] | solvent B [%] |
|---|---|
| 0.00 | 60 |
| 3.00 | 20 |
| 4.00 | 20 |
| 4.30 | 60 |
| 6.10 | 60 |

Differential Scanning Calorimetry (DSC)

Instrument: Mettler Toledo DSC 822E coupled with a Mettler Toledo Gas-Flow-Controller TS0800GC1 (Mettler-Toledo GmbH, Gießen, Germany)
Aluminium crucible: 40 µL
Lid: Perforated
Temperature range: 30° C. to 350° C.
Heating rate: 10° C./min
Nitrogen flush: 50 mL/min
Software: STARe Version. 8.10
Interpretation: Endothermic modus X-Ray Powder Diffraction (XRPD)

The sample was analyzed on a D8 Advance X-ray powder diffractometer (Bruker-AXS, Karlsruhe, Germany). The sample holder was rotated in a plane parallel to its surface at 20 rpm during the measurement. Further conditions for the measurements are summarized in the table below. The raw data were analyzed with the program EVA (Bruker-AXS, Germany). The samples were layered onto a silicon specimen holder.

| | standard measurement |
|---|---|
| radiation | Cu K$_\alpha$ (λ = 1.5406 Å) |
| source | 38 kV/40 mA |
| detector | Vantec |
| detector slit | Variable |

| | standard measurement |
|---|---|
| divergence slit | v6 |
| antiscattering slit | v6 |
| 2θ range/° | 2 ≤ 2θ ≤ 55 |
| step size/° | 0.017 |

Example 1: Preparation of Ibrutinib Hydrochloride (IBT HCL) by Conventional Processes (Experiments 1 and 2) and by Processes According to the Present Invention (Experiments 3 Through 6)

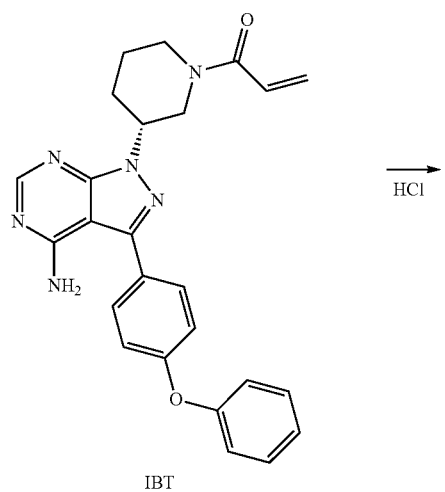

IBT

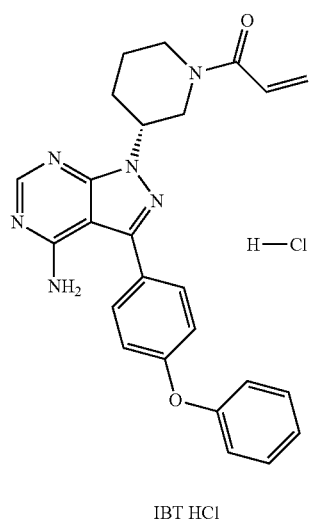

IBT HCl

Experiment 1

2.0 g (4.54 mmol) ibrutinib (IBT) base were dissolved in 10 ml dichloromethane (DCM) followed by addition of 20 ml methyl tert.-butylmethylether (MTBE). While stirring at RT (22° C.), 3.41 mL (6.8 mmol) 2 N HCl in diethylether (Et$_2$O) were added and stirring was continued for 30 min. After addition of another 20 ml MTBE, the formation of a fine white precipitate that shortly later converted into a sticky viscous semisolid. Solidification was induced by sonication and the resulting lumps were scraped off the glass wall using a spatula. The coarse suspension was stirred overnight at room temperature. The solids were filtered off, washed with 20 ml MTBE and dried 24 h at 40° C./10 mbar.

Yield: 2.07 g (95.6%)

Chemical purity: 94% (peak area at λ=230 nm and 254 nm).

Prominent impurity (IBT impurity compound of formula (II)): 5.1/4.7% (peak area at λ=230 nm and 254 nm);

Experiment 2

15.0 g (34.1 mmol) IBT base were dissolved in 75 ml DCM. While stirring at RT (22° C.), 25.5 mL (51.1 mmol) 2 N HCl in Et$_2$O were added. After completion, the mixture was cooled to 0° C., followed by addition of 200 ml MTBE. Using a rotary evaporator, the volume was reduced to approx. 200 ml, another 150 ml MTBE was added and the mixture was stirred for 3 h at 50° C. The intermittently viscous semisolid converted into a solid, which was firmly attached to the inner glass wall of the flask. The solid was scraped off and the suspension was stirred for another 3 h. The solid was filtered off, washed with 100 ml MTBE and dried 24 h at 40° C./10 mbar.

Yield: 16.1 g (99.1%)

Chemical purity: 96% (peak area at λ=230 nm and 254 nm).

IBT impurity (compound of formula (II)): 4.0/3.7% (peak area at λ=230 nm and 254 nm);

Experiment 3

5 g (11.4 mmol) IBT base was dissolved in 20 mL DCM. The solution was cooled to −10° C. and 3.4 mL (13.6 mmol) 4 N HCl in dioxane was added. The clear solution was stirred for 10 min followed by dropwise addition of 200 ml MTBE over a period of 100 min, while keeping the temperature below 0° C. After completion, the fine white suspension was allowed to warm to RT and stirring was continued for 18 h. The solid was filtered off, washed with 50 ml MTBE and dried 24 h at 40° C./10 mbar.

Yield: 4.95 g (91.4%)

Chemical purity: 99.4/>99.9% (peak area at λ=230 nm and 254 nm).

IBT impurity (compound of formula (II)): 0.4/<0.1% (peak area at λ=230 nm and 254 nm);

Experiment 4

25 g (56.8 mmol) IBT base were dissolved in 100 ml DCM. The solution was cooled to −10° C. and 17 ml (68.1 mmol) 4 N HCl in dioxane were added. The clear solution was stirred for 10 min followed by dropwise addition of 1 L MTBE over a period of 100 min, while keeping the temperature below +2° C. After completion, the fine white suspension was allowed to warm to RT and stirring was continued for 18 h. The solid was filtered off, washed with 200 ml MTBE and dried 24 h at 40° C./10 mbar.

Yield: 26.2 g (96.8%)

Chemical purity: 99.8/99.9% (peak area at λ=230 nm and 254 nm).

IBT impurity (compound of formula (II)): 0.10/<0.1% (peak area at λ=230 nm and 254 nm);

Experiment 5

30 g (68.1 mmol) IBT base were dissolved in 120 mL DCM. The solution was cooled to −20° C. and 57 mL (71.5 mmol) 1.25 N HCl in isopropanol were added. The clear solution was stirred for 10 min followed by dropwise addition of 1500 ml MTBE over a period of 3 h, while keeping the temperature below −10° C. After completion, the mixture was allowed to warm to RT and stirring was continued for 40 h. The resulting fine white solid was filtered off, washed with 300 ml MTBE and dried 24 h at 50° C./10 mbar.

Yield: 30.1 g (92.4%)

Chemical purity: 99.7/99.8% (peak area at λ=230 nm and 254 nm).

IBT impurity (compound of formula (II)): <0.1% (peak area at λ=230 nm and 254 nm);

Experiment 6

3 g (6.81 mmol) IBT base were dissolved in 4 mL DCM. The solution was cooled to −20° C. and 5.7 mL (7.15 mmol) 1.25 N HCl in isopropanol (iPrOH) were added. The clear solution was stirred for 10 min followed by dropwise addition of 30 ml iPrOH, while keeping the temperature below −10° C. After completion, the mixture was allowed to warm to RT and stirring was continued for 18 h. The resulting fine white solid was filtered off, washed with 10 ml iPrOH and dried 24 h at 50° C./10 mbar.

Yield: 2.90 g (89.3%)

Chemical purity: 99.9/99.9% (peak area at λ=230 nm and 254 nm).

IBT impurity (compound of formula (II)): <0.1% (peak area at λ=230 nm and 254 nm);

The results of Experiments 1 through 6 are summarized below

|  | Exp 1 | Exp 2 | Exp 3 | Exp 4 | Exp 5 | Exp 6 |
| --- | --- | --- | --- | --- | --- | --- |
| Ibrutinib base in g | 2.0 | 15.0 | 5.0 | 25.0 | 30.0 | 3.0 |
| HCl, dissolved in | 2N in diethylether | 2N in diethylether | 4N in dioxane | 4N in dioxane | 1.25N in isopropanol | 1.25N in isopropanol |
| HCl excess in eq. | 1.5 | 1.5 | 1.2 | 1.2 | 1.05 | 1.05 |
| reaction temperature in ° C. | 22 | 22 | −10 | −10 | −20 | −20 |
| solvent | dichloromethane | dichloromethane | dichloromethane | dichloromethane | dichloromethane | dichloromethane |
| antisolvent | MTBE | MTBE | MTBE | MTBE | MTBE | isopropanol |
| yield in g | 2.07 | 16.1 | 4.95 | 26.2 | 30.1 | 2.90 |
| yield in % | 95.6 | 99.1 | 91.4 | 96.8 | 92.4 | 89.3 |
| purity in % | 94.0 | 96.0 | 99.4 | 99.8 | 99.7 | 99.9 |

Figure 7:
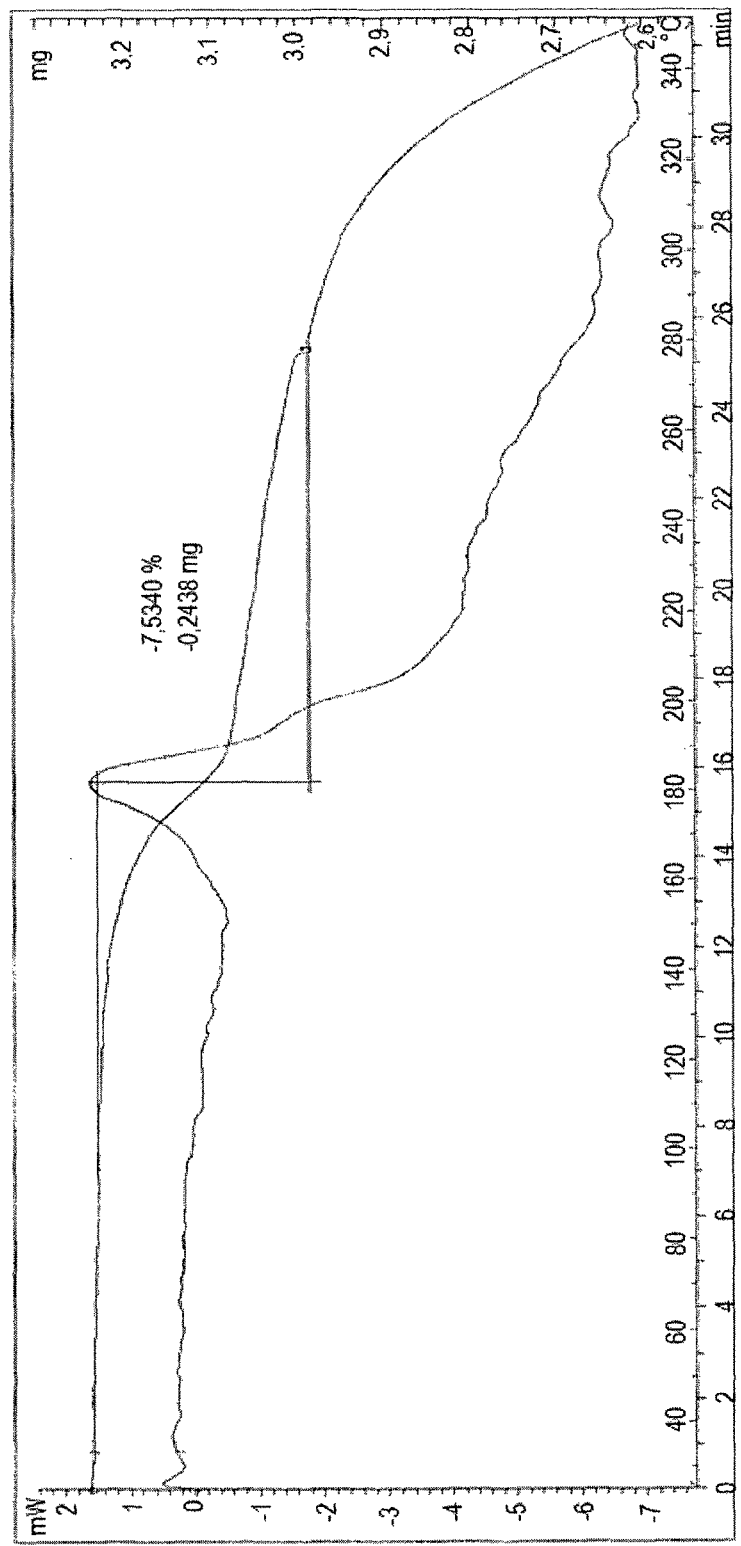
FIG. 7 shows the TGA spectrum of crystalline ibrutinib hydrochloride.

The quantitative conversion of ibrutinib into ibrutinib hydrochloride is verified by means of $^1$H-NMR overlay indicating a complete shift of the pyrimidinium proton from 8.24 ppm to 8.57 ppm (cf. FIG. 1a) and thermogravimetric analysis (cf. FIG. 7).

Comparison of solubilities of ibrutinib hydrochloride in pH values which are relevant for the gastrointestinal tract

| | solubility in mg/ml | | | | | | | | |
| --- | --- | --- | --- | --- | --- | --- | --- | --- | --- |
| | pH 1.2 (0.1M HCl) | | | pH 4.5 (20 mMol NaAc) | | | pH 6.8 (50 mMol KH$_2$PO$_4$) | | |
| | 15 min | 1 h | 24 h | 15 min | 1 h | 24 h | 15 min | 1 h | 24 h |
| base | 2.07 | 2.64 | 2.64 | 0.01 | 0.01 | 0.01 | 0.01 | 0.01 | 0.01 |
| HCl | 7.37 | 7.72 | 7.38 | 0.01 | 0.02 | 0.46 | 0.01 | 0.05 | 0.41 |

Example 2: Preparation of Compound Formula (II)

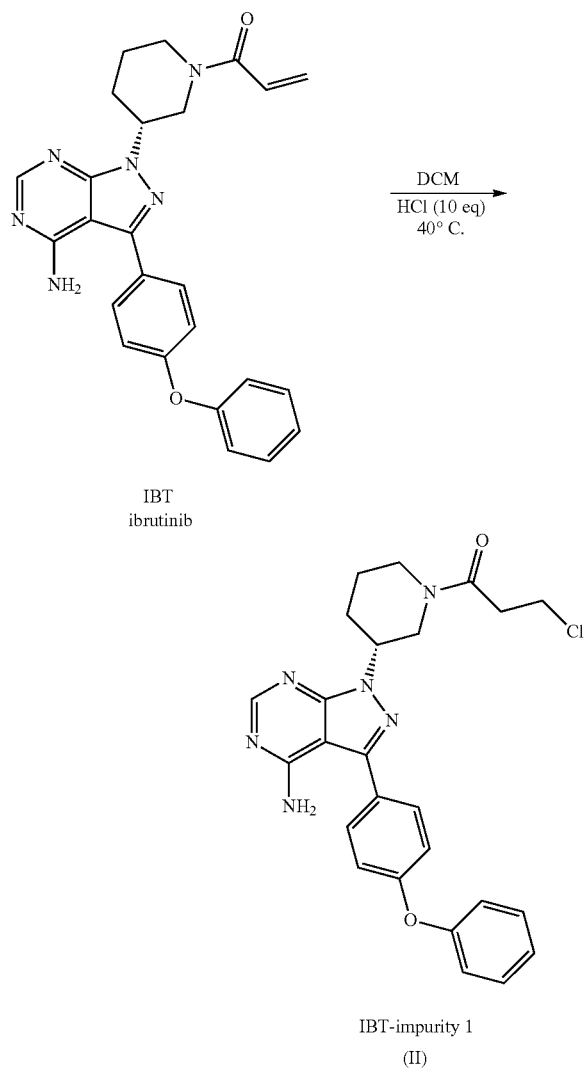

IBT
ibrutinib

IBT-impurity 1
(II)

At RT, 50 mg (0.11 mmol) IBT base was dissolved in 1.0 ml DCM. After addition of 0.57 ml (1.1 mmol) 2N HCl in Et$_2$O, the mixture was briefly sonicated and warmed to 40° C. The formation of IBT impurity (compound of formula (II)) was monitored by HPLC/UV. After 26 h, IBT impurity 1 was isolated in 97% chemical purity ([area-%] at λ=230/254 nm).

Example 3: Comparison of Ibrutinib Acid Addition Salt Preparations

Experiments were carried out with hydrochloric acid, hydrobromic acid, sulfuric acid, methanesulfonic acid, ethanedisulfonic acid and phosphoric acid according to the following general methods:

Method I:
1 eq Ibrutinib (IBT) base was dissolved in 28 eq. dichloromethane (DCM). The clear solution was cooled to −20° C. before 1.05 eq of the corresponding acid (1.25 M in iPrOH) was added. The solution was stirred for 5 min followed by addition of 190 eq. tert.-butylmethylether (MTBE). After completion the resulting slurry was allowed to reach room temperature and stirring was continued for 24 h. The obtained precipitate was filtered off, washed with MTBE and dried under reduced pressure to yield the corresponding acid addition salt.

Method II:
1 eq Ibrutinib (IBT) base was dissolved in 14 eq. dichloromethane (DCM). The clear solution was cooled to 6-10° C. before 1.05 eq of the corresponding acid (1.25 M in iPrOH) was added. The solution was stirred for 5 min followed by addition of 150 eq. isopropanol (iPrOH). After completion the resulting mixture was allowed to reach room temperature and stirring was continued for 24 h. The obtained precipitate was filtered off, washed with isopropanol and dried under reduced pressure to yield the corresponding acid addition salt.

It was demonstrated that both procedures yield identical results regarding the chemical purity (≥99.8%) and the morphological state. An overview of the applied acids and the resulting solid state is given in the table below.

| applied acid | pKa(1) | pKa(2) | acid addition salt | morphology |
| --- | --- | --- | --- | --- |
| hydrobromic acid | −9.00 | | ibrutinib bromide | crystalline |
| hydrochloric acid | −6.00 | | ibrutinib chloride | crystalline |
| sulfuric acid | −3.00 | 1.99 | ibrutinib hydrogensulfate | amorphous |
| ethanedisulfonic acid | −2.06 | −1.50 | ibrutinib hemi edisylate | amorphous |
| methanesulfonic acid | −1.90 | | ibrutinib mesylate | amorphous |
| phosphoric acid | 2.15 | | ibrutinib base | — |

Figure 10:
FIG. 10 shows an XRPD pattern of amorphous ibrutinib methylsulfonate.
Figure 11:
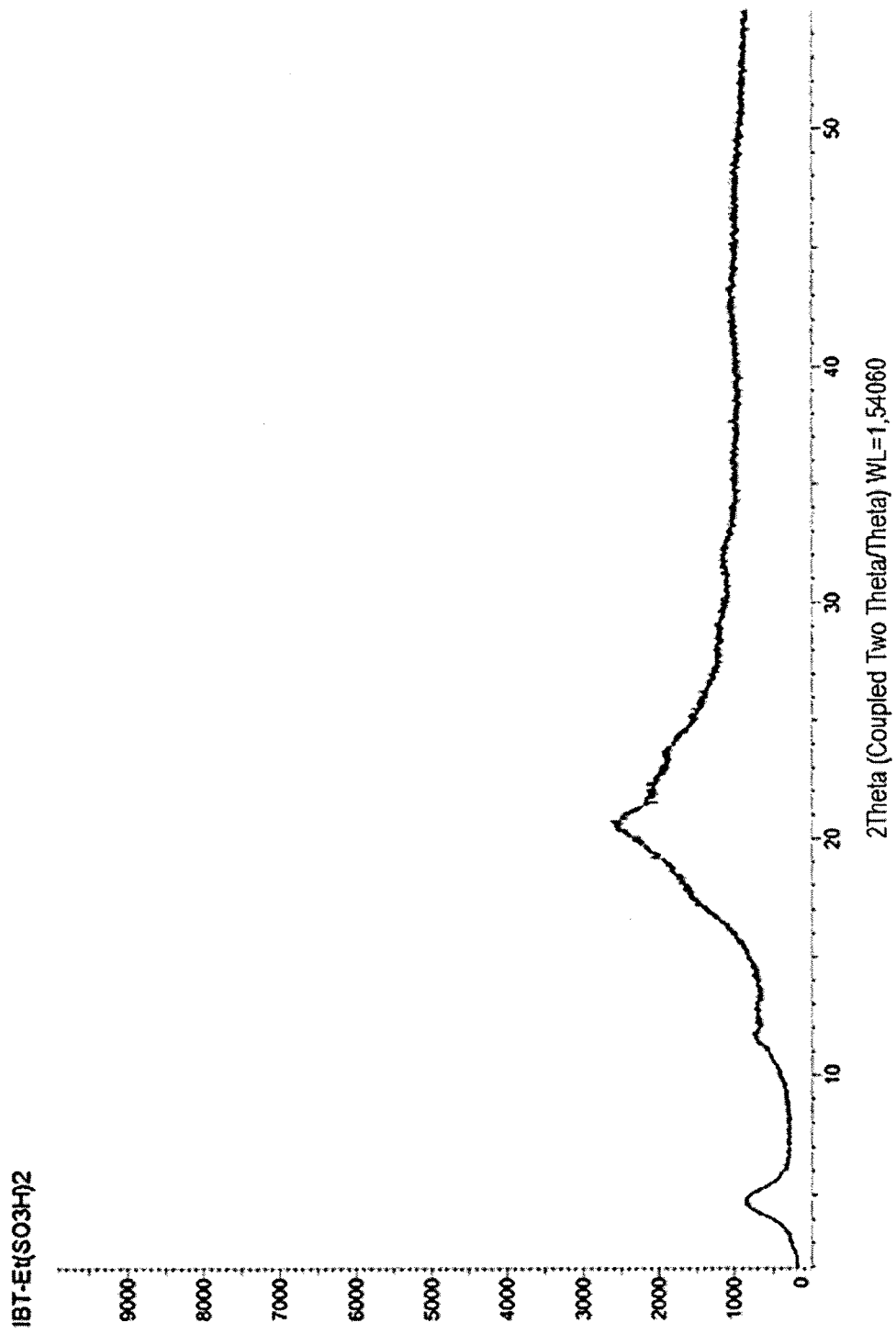
FIG. 11 shows an XRPD pattern of amorphous ibrutinib ethane disulfonate.
Figure 12:
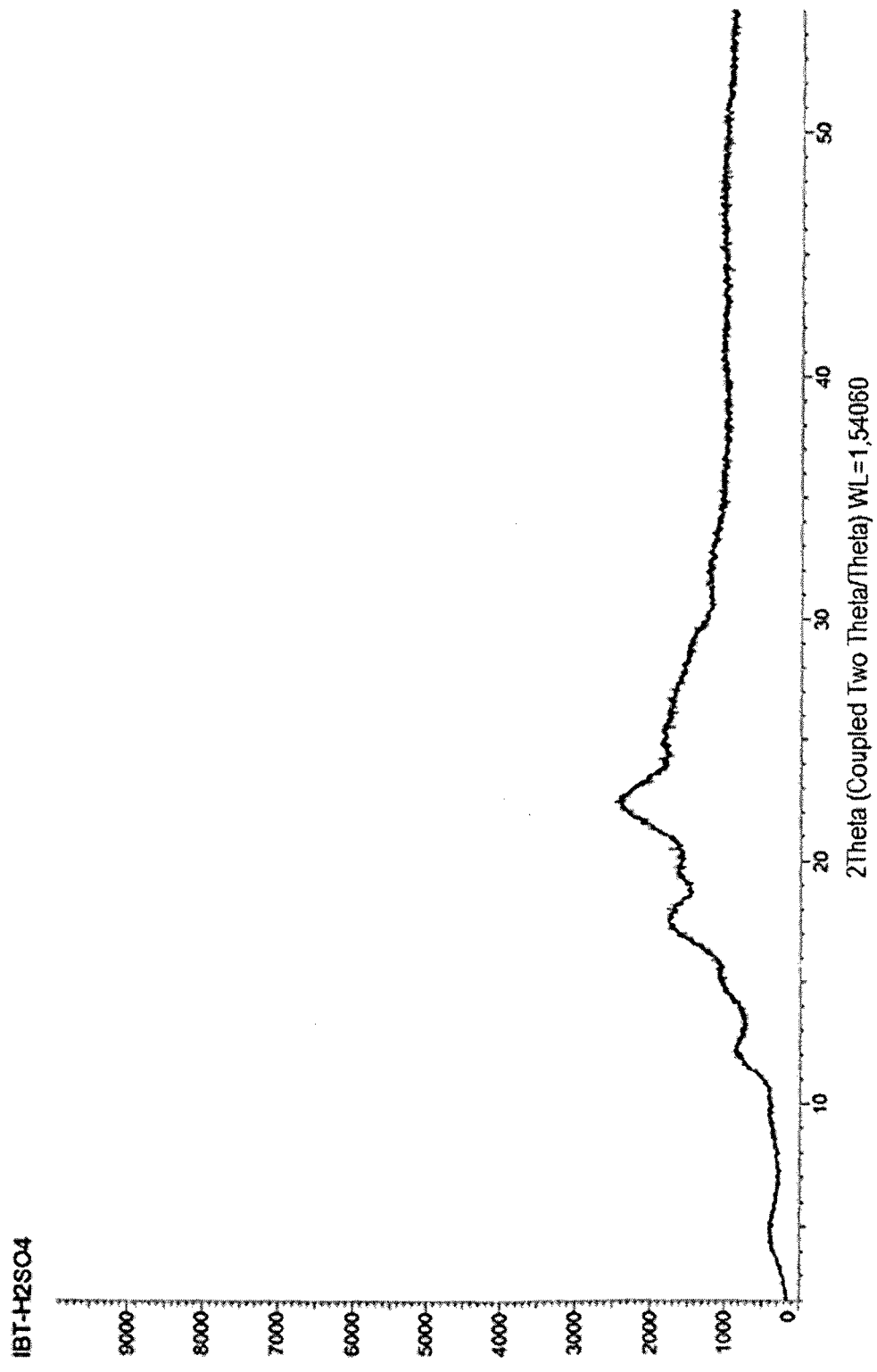
FIG. 12 shows an XRPD pattern of amorphous ibrutinib sulfonate.

FIGS. 10 to 12 show that reacting ibrutinib with any of methanesulfonic acid, ethanedisulfonic acid or sulfuric acid leads to acid addition salts with amorphous morphology.

Figure 1B:
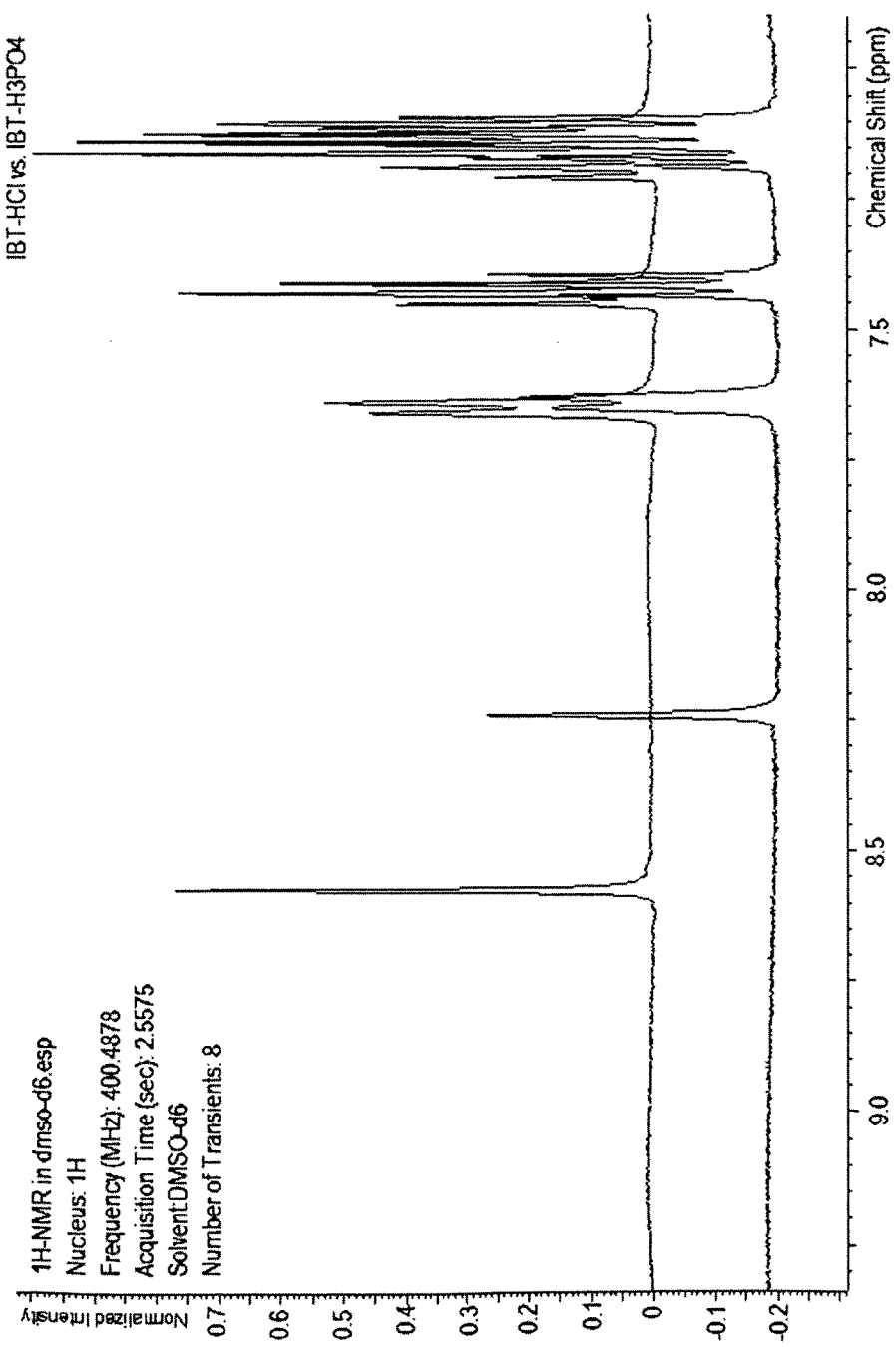
FIG. 1b shows a zoomed cutout of the $^1$H-NMR spectrum of ibrutinib hydrochloride (upper graph) compared to the presumed $^1$H-NMR spectrum of ibrutinib phosphate (lower graph) ($^1$H-NMR in DMSO-$d_6$, 400 MHz).

Further, not wishing to be bound to theory it seems that acid addition salts can be obtained when an acid with a pKa lower than approximately 2 is applied. FIG. 1b illustrates that application of phosphoric acid does not convert ibrutinib into a salt, due to the missing shift of pyrimidinium proton at 8.24 ppm to 8.57 ppm in the $^1$H-NMR spectrum as it is the case for example with hydrochloric acid (compare also with FIG. 1a).

X-Ray Powder Diffraction Results (XRPD)

The acid addition product ibrutinib HCl and ibrutinib HBr, as obtained by the above described procedures were characterized by means of x-ray powder diffraction. It is shown in FIGS. 3 and 9, respectively.

The x-ray powder diffractogram of ibrutinib HCl is characterized by the following peaks: 9.8, 13.6, 15.1, 17.0 and 21.1 degrees 2-theta±0.2 degrees 2-theta or 9.8±0.1°2-θ, 15.3±0.1°2-θ, 21.1±0.1°2-θ, 22.6±0.1°2-θ and 24.3±0.1°2-θ. Further characteristic peaks are at 8.1, 8.2, 14.2, 19.9 and 28.9 degrees 2-theta±0.2 degrees 2-theta or 13.6±0.1°2-θ, 16.5±0.1°2-θ, 17.0±0.1°2-θ, 25.5±0.1°2-θ and 28.9±0.1°2-θ.

The complete list of XRPD diffraction peaks of ibrutinib hydrochloride:

| degrees 2-theta ± 0.2 degrees 2-theta | relative intensity |
| --- | --- |
| 8.1 | 6.9% |
| 8.2 | 13.8% |
| 9.1 | 1.9% |
| 9.8 | 45.0% |
| 10.7 | 3.0% |

| degrees 2-theta ± 0.2 degrees 2-theta | relative intensity |
|---|---|
| 11.3 | 7.0% |
| 11.5 | 13.7% |
| 13.6 | 38.5% |
| 14.1 | 11.2% |
| 14.2 | 20.9% |
| 15.1 | 32.9% |
| 15.3 | 56.3% |
| 15.6 | 24.7% |
| 16.5 | 27.5% |
| 17.0 | 44.0% |
| 17.3 | 16.1% |
| 18.5 | 23.2% |
| 19.9 | 26.3% |
| 20.9 | 16.4% |
| 20.4 | 16.8% |
| 20.6 | 28.1% |
| 20.8 | 19.9% |
| 21.1 | 100.0% |
| 22.2 | 33.6% |
| 22.6 | 76.3% |
| 22.6 | 66.4% |
| 23.1 | 30.4% |
| 23.1 | 27.3% |
| 23.6 | 12.2% |
| 23.8 | 19.2% |
| 24.3 | 97.0% |
| 25.6 | 26.9% |
| 25.5 | 59.1% |
| 25.7 | 11.7% |
| 28.6 | 34.9% |
| 29.0 | 36.4% |
| 28.9 | 40.2% |
| 29.4 | 29.7% |
| 29.7 | 11.1% |
| 32.0 | 12.4% |
| 32.2 | 14.2% |
| 32.7 | 12.8% |

The x-ray powder diffractogram of ibrutinib H Br is characterized by the following peaks: 5.5, 18.1, 22.3, 24.5 and 26.9 degrees 2-theta±0.2 degrees 2-theta. Further characteristic peaks are at 12.3, 15.6, 18.3, 20.2, 21.6° and 24.4°. degrees 2-theta±0.2 degrees 2-theta The complete list of XRPD diffraction peaks of ibrutinib hydrobromide:

| degrees 2-theta ± 0.2 degrees 2-theta | relative intensity |
|---|---|
| 5.5 | 18.6% |
| 10.6 | 4.5% |
| 11.1 | 3.3% |
| 12.3 | 6.1% |
| 12.7 | 2.0% |
| 14.8 | 6.7% |
| 15.6 | 16.5% |
| 16.0 | 11.6% |
| 16.6 | 15.7% |
| 18.1 | 39.2% |
| 18.3 | 15.1% |
| 19.1 | 2.8% |
| 20.2 | 23.2% |
| 21.6 | 15.9% |
| 22.3 | 100.0% |
| 23.0 | 11.8% |
| 24.4 | 18.0% |
| 24.5 | 34.7% |
| 24.7 | 8.7% |
| 25.6 | 10.2% |
| 26.9 | 22.3% |
| 27.4 | 6.9% |
| 29.3 | 6.1% |
| 29.5 | 9.7% |
| 29.6 | 8.6% |
| 31.8 | 11.0% |
| 33.6 | 7.0% |
| 33.7 | 5.3% |
| 36.0 | 6.1% |
| 37.0 | 7.7% |
| 38.7 | 6.9% |
| 39.9 | 5.2% |
| 41.2 | 10.3% |
| 48.2 | 7.9% |

The invention claimed is:

1. A crystalline acid addition salt of ibrutinib having a purity of at least 99.0%.

2. The acid addition salt of claim 1, wherein the acid is hydrochloric acid or hydrobromic acid.

3. An acid addition salt of ibrutinib, wherein the content of an addition reaction product of the acid with the acrylic double bond of ibrutinib is lower than 1% by weight.

4. The acid addition salt of ibrutinib according to claim 3, wherein the content of the addition reaction product is lower than 0.5% by weight.

5. The acid addition salt according to claim 3, wherein the acid addition salt of ibrutinib is crystalline ibrutinib hydrochloride, which shows an XRPD pattern having peaks at 9.8±0.1°2-Theta, 15.3±0.1°2-Theta, 21.1±0.1°2-Theta, 22.6±0.1°2-Theta and 24.3±0.1°2-Theta.

6. The crystalline addition salt of ibrutinib according to claim 3, wherein the content of the addition reaction product is lower than 0.2% by weight.

7. The crystalline addition salt of ibrutinib according to claim 3, wherein the content of the addition reaction product is lower than 0.1% by weight.

8. A method of preparing an acid addition salt of ibrutinib as defined in claim 1, said method comprising the steps of:
   a. dissolving ibrutinib in a suitable solvent to obtain a solution, and
   b. contacting the obtained solution with the acid, characterized in that during the step of adding the acid, the solution is cooled below room temperature (22° C.).

9. The method according to claim 8, which method further comprises the step of c) precipitating the acid addition salt in a suitable antisolvent.

10. The method according to claim 9, wherein the solution is cooled to below 10° C. in steps b) and/or c).

11. The method according to claim 10, wherein the acid is hydrogen chloride.

12. A pharmaceutical composition comprising an acid addition salt of ibrutinib according to claim 1.

13. The method according to claim 8, wherein the suitable solvent of step (a) is an organic solvent.

14. The method according to claim 9, wherein the solution is cooled to below 0° C. in steps b) and/or c).

* * * * *